(12) United States Patent
Macina

(10) Patent No.: US 7,014,996 B1
(45) Date of Patent: Mar. 21, 2006

(54) METHOD OF DIAGNOSING, MONITORING, STAGING, IMAGING AND TREATING GYNECOLOGIC CANCERS

(75) Inventor: Roberto A. Macina, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/806,302

(22) PCT Filed: Sep. 30, 1999

(86) PCT No.: PCT/US99/22753

§ 371 (c)(1),
(2), (4) Date: Jul. 19, 2001

(87) PCT Pub. No.: WO00/20044

PCT Pub. Date: Apr. 13, 2000

Related U.S. Application Data

(60) Provisional application No. 60/102,743, filed on Oct. 2, 1998.

(51) Int. Cl.
| | | |
|---|---|---|
| C12Q 1/68 | (2006.01) | |
| C12Q 1/00 | (2006.01) | |
| C12Q 33/53 | (2006.01) | |
| C12Q 33/567 | (2006.01) | |
| C12Q 33/574 | (2006.01) | |

(52) U.S. Cl. ............................. 435/6; 435/4; 435/7.1; 435/7.21; 435/7.23; 436/63; 436/64

(58) Field of Classification Search .................. 435/4, 435/6, 7.1, 7.21, 7.23, 7.2; 436/63, 64
See application file for complete search history.

(56) References Cited

U.S. PATENT DOCUMENTS

| | | | |
|---|---|---|---|
| 6,066,724 A | 5/2000 | Ni et al. | |
| 6,174,992 B1 | 1/2001 | Ni et al. | |
| 6,228,596 B1 | 5/2001 | Macina et al. | |
| 2002/0034739 A1 * | 3/2002 | Lehrer et al. | |

FOREIGN PATENT DOCUMENTS

| | | |
|---|---|---|
| EP | 1033401 A2 | 9/2000 |
| WO | WO 96/38463 | 12/1996 |
| WO | WO 96/38463 A1 | 12/1996 |
| WO | WO 97/34997 | 9/1997 |
| WO | WO 97/34997 A1 | 9/1997 |
| WO | WO 98/07857 A1 | 2/1998 |
| WO | WO 98/21331 A1 | 5/1998 |
| WO | WO 98/35229 A1 | 8/1998 |
| WO | WO 98/56248 A1 | 12/1998 |
| WO | WO 99/19487 A1 | 4/1999 |
| WO | WO 99/45147 A1 | 9/1999 |
| WO | WO 99/47669 A2 | 9/1999 |
| WO | WO 99/53051 A2 | 10/1999 |
| WO | WO 99/54461 A2 | 10/1999 |
| WO | WO 99/63088 A2 | 12/1999 |
| WO | WO 00/20043 A1 | 4/2000 |
| WO | WO 00/20044 A1 | 4/2000 |
| WO | WO 00/20447 A2 | 4/2000 |
| WO | WO 00/32221 A2 | 6/2000 |
| WO | WO 00/35950 A2 | 6/2000 |
| WO | WO 00/41516 A2 | 7/2000 |
| WO | WO 00/60076 A2 | 10/2000 |
| WO | WO 00/73454 A1 | 12/2000 |
| WO | WO 01/40466 A2 | 6/2001 |

OTHER PUBLICATIONS

Shantz and Pegg, Int J of Biochem and Cell Biol., 1999, vol. 31, pp. 107-122.*
McClean and Hill, Eur J of Cancer, 1993, vol. 29A, pp. 2243-2248.*
Fu et al, EMBO Journal, 1996, vol. 15, pp. 4392-4401.*
Watson et al., "Mammaglobin, a Mammary-specific member of the Uteroglobin Gene Family, Is Overexpressed in Human Breast Cancer[1]", Cancer Research 1996 56:860-865.
Koshiyama et al., "Expression of pS2 Protein in Endometrial Carcinomas:Correlation with Clinicopathologic Features and Sex Steriod Receptor status", *Int. J. Cancer* 1997 74:237-244.
Sasano et al., "Adrenal 4-Binding Protein in Common Epithelial and Metastatic Tumors of the Ovary", *Human Pathology* 1996 27:595-598.
Schmitt et al., "Time-varying prognostic impact of tumour biological factors urokinase (uPA), PAI-2 and steroid hormone receptor status in primary breast cancer", *British J. Of Cancer* 1997 76(3):306-311.
Tardivel-Lacombe et al., "Immunohistochemical Detection of the Sex Steroid-Binding Plasma Protein in Human Mammary Carcinoma Cells", *Biochem. Biophys. Res. Commun.* 1984 118:488-494.
Parker et al., Prostatic steroid binding protein: gene duplication and steroid binding. Nature. Jul. 1, 1982; vol. 298:92-94.
Database EMBASE on STN, Elsevier Sci. B.V., Shina et al. Immunohistochemical analysis of estramustine binding protein with particular reference to proliferative activity in human prostatic carcinoma, abstract, Prostate, 1997, vol. 32(1):49-58.
Aoki et al., Isolation of human uterglobin from blood filtrate. Mol. Hum. Repro. 1996; vol. 2(7):489-497.

(Continued)

*Primary Examiner*—Alana M. Harris
(74) *Attorney, Agent, or Firm*—Licata & Tyrrell P.C.; Nathan P. Letts

(57) ABSTRACT

The present invention provides a new method for detecting, diagnosing, monitoring, staging, prognosticating, imaging and treating gynecologic cancers including uterine, breast, endometrial and ovarian cancer.

9 Claims, No Drawings

OTHER PUBLICATIONS

Becker et al., Identification of mammaglobin B, a novel member of the uteroglobin gene family. Genomics. 1998; vol. 54:70-78.

Chilton et al., Zinc finger proteins RUSH in where others fear to tread. Biol. Of Reprod. 1998; vol. 58:285-294.

Claessens et al., Sequence-specific binding of androgen-receptor complexes to prostatic binding protein genes. Mol. Cell. Endo. 1990; vol. 74:203-212.

Claessens et al., Intronic androgen response elements of prostatic binding protein genes. BBRC. Mar. 15, 1993; vol. 191(2):688-694.

Claessens et al., Functional androgen response elements in the genes coding for prostatic binding protein. Annals NY Acad. Sci. 1993; vol. 684:199-201.

Colpitts et al., Mammaglobin is found in breast tissue as a complex with BU101. Biochemistry. 2001; vol. 40:11048-11059.

Gow, Alexander, Redefining the lipophilin family of proteolipid proteins. J. Neurosci. Res. 1997; vol. 50:659-664.

Koshiyama et al., Expression of pS2 protein in Endometrial carcinomas: correlation with clinicopathological features and sex steroid receptor status. Int. J. Cancer. 1997; vol. 74:237-244.

Lehrer et al., Lipophilin, a novel heterodimeric protein of human tears. FEBS Letters. 1998; vol. 432:163-167.

Lehrer et al., Secretory lipophilins: A tale of two species. Annals NY Acad. Sci. 2000; vol. 923:59-67.

Maroulakou et al., Prostate and mammary adenocarcinoma in transgenic mice carrying a rat C3(1) simian virus 40 large tumor antigen fusion gene. PNAC. Nov. 1994; vol. 91:11236-11240.

Ni et al., All human genes of the uterglobin family are localized on chromosome 11q12.2 and form a dense cluster. Annals NY Acad. Sci. 2000; vol. 923:25-42.

Sasano et al., Adrenal 4-binding protein in common epithelial and metastatic tumors of the ovary. Human Pathology. Jun. 1996; vol. 27(6):595-598.

Scholz et al., Hormone-induced recruitment od Sp1 mediates estrogen activation of rabbit uterglobin gene in Endometrial epithelium. JBC. Feb. 20, 1998; vol. 273(8):4360-4366.

Schmitt et al., Time varying prognostic impact of tumor biological factors urokinase (uPA), PAI-1 and steroid hormone receptor status primary breast cancer. British J. Cancer. 1997; vol. 76(3):306-311.

Shao et al., Prostatein $C_3$-mRNA: a sensitive marker of androgen-responsiveness in prostate explant cultures. The Prostate. 1990; vol. 17:41-55.

Shibata et al., Altered expression of transforming growth factor βs during urethral and bulbourethral gland tumor progression in transgenic mice carrying that androgen-responsive C3(1) 5' flanking region fused to SV40 large T antigen. Carcinogenesis. 1998; vol. 19(1):195-205.

* cited by examiner

METHOD OF DIAGNOSING, MONITORING, STAGING, IMAGING AND TREATING GYNECOLOGIC CANCERS

Which claims the benefit of U.S. Provisional application Ser. No. 60/102,743, filed Oct. 2, 1998.

FIELD OF THE INVENTION

This invention relates, in part, to newly developed assays for detecting, diagnosing, monitoring, staging, prognosticating, imaging and treating cancers, particularly gynecologic cancers including endometrial, mammary, ovary and uterine cancer.

BACKGROUND OF THE INVENTION

In women, gynecologic cancers account for more than one-fourth of the malignancies.

For example, endometrial cancer occurs at a rate of approximately 44,500 new cases per year with approximately 10,000 deaths per year. If diagnosed and treated early, when the cancer is still confined to the endometrium, cure can be achieved in approximately 95% of the cases by hysterectomy. Pap smears can show endometrial cancers but are effective in only 50% of the cases. For the remainder, abnormal vaginal bleeding is typically the first clinical sign of endometrial cancer.

Sarcoma of the uterus, a very rare kind of cancer in women, is a disease in which cancer (malignant) cells start growing in the muscles or other supporting tissues of the uterus. Sarcoma of the uterus is different from cancer of the endometrium, a disease in which cancer cells start growing in the lining of the uterus. Women who have received therapy with high-dose x-rays (external beam radiation therapy) to their pelvis are at a higher risk to develop sarcoma of the uterus. These x-rays are sometimes given to women to stop bleeding from the uterus. Like most cancers, sarcoma of the uterus is best treated when it is found (diagnosed) early. Sarcoma of the uterus usually begins after menopause. When a patient has signs of such cancer, an internal pelvic examination is usually performed to detect any lumps or changes in shape of the pelvic organs. A Pap test may also be performed, however because sarcoma of the uterus begins inside the organ, this cancer is not usually detected by the Pap test. A dilation and curettage (D&C) may also be performed and a biopsy sample taken and examined microscopically.

It is estimated that one of every nine women in America will develop breast cancer sometime during her life based on a lifespan of 85 years. Annually, over 180,000 women in the United States are diagnosed with breast cancer and approximately 46,000 die from this disease. Every woman is at risk for breast cancer. However, a woman's chances of developing breast cancer increase as she grows older; 80 percent of all cancers are found in women over the age of 50. There are also several risk factors that can increase a woman's chances of developing breast cancer. These include a family history of breast cancer, having no children or the first child after the age of 30, and an early start of menstruation. However, more than 70 percent of women who develop breast cancer have no known risk factors. Less than 10 percent of breast cancer cases are thought to be related to the BRCA1 gene discovered in 1994. Researchers are now investigating the role of other factors such as nutrition, alcohol, exercise, smoking, and oral contraceptives in development of this gynecologic cancer. Mammograms, or special x-rays of the breast, can detect more than 90 percent of all cancers.

Carcinoma of the ovary is another very common gynecologic cancer. In fact, ovarian cancer causes more deaths than any other cancer of the female reproductive system. Approximately one in 70 women develop ovarian cancer during their lifetime. An estimated 14,500 deaths in 1995 resulted from ovarian cancer. Ovarian cancer often does not cause any noticeable symptoms. Possible warning signals include an enlarged abdomen due to an accumulation of fluid or vague digestive disturbances (discomfort, gas or distention) in women over 40. In rare cases abnormal vaginal bleeding also occurs. Pap tests do not detect ovarian cancer. Thus, periodic, complete pelvic examinations are important and recommended annually for women over 40.

In all of these gynecologic cancers, chances of survival are much better if the cancer is diagnosed at an early stage. Further, treatment decisions for the individual are linked to the stage of the cancer present in that individual. However, current cancer staging methods are limited and some such cancers initially staged as not metastatic are actually metastatic. Discovery of metastasis is significant because patients with metastatic cancers have a poorer prognosis and require significantly different therapy than those with localized cancers.

Accordingly, there is a great need for sensitive and accurate methods for early detection and staging of gynecologic cancers such as endometrial, breast, uterine and ovarian cancer in a human to determine whether or not such cancer has metastasized and for monitoring the progress of such cancer in a human which has not metastasized for the onset of metastasis.

Steroid binding proteins, including uteroglobin and CC10, are a class of proteins which bind steroids along with methylsulfonyl metabolites of polychlorinated biphenyls. The exact function of members of this class of protein is uncertain. However, uteroglobin has been shown to inhibit $PLA_2$ mediated responses.

Gene and gene products homologous to uteroglobin are described in WO 97/34997 entitled Human Endometrial Specific Steroid Binding Factors I, II and III. The genes and their encoded products are referred to as Human Endometrial Specific Steroid-Binding Factors I, II and III (hESF I, II, and III). Methods for utilizing these genes and gene products in research and diagnostic and clinical arts are disclosed. In particular, methods for detecting mutations in the hESFI, II or III gene or altered protein expression resulting from a mutant gene are indicated to be useful in diagnosing susceptibility to asthma and endometrial cancer.

A gene and gene product homologous to uteroglobin and very similar to hESF III, referred to as human mammoglobin homolog or HGH, is also described in WO 99/19487. The human mammoglobin homolog is suggested to be useful for the diagnosis, prevention and treatment of neoplastic disorders and endometriosis.

It has now been found that detection of hESF III, referred to herein as ESBPIII, is useful in diagnosing, monitoring, staging, prognosticating, imaging and treating cancers, particularly gynecologic cancers including endometrial, mammary, ovary and uterine cancer.

Accordingly, in the present invention, methods are provided for detecting, diagnosing, monitoring, staging, prognosticating, imaging and treating gynecologic cancers via ESBPIII. ESBPIII refers, among other things, to native protein expressed by the gene comprising the polynucleotide sequence of SEQ ID NO:1. The amino acid sequence of a polypeptide encoded by SEQ ID NO:1 is depicted herein as SEQ ID NO:2. In the alternative, what is meant by the ESBPIII as used herein, means the native mRNA encoded by the gene comprising the polynucleotide sequence of SEQ ID NO:1 or levels of the gene comprising the polynucleotide sequence of SEQ ID NO:1.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of gynecologic cancers by analyzing for changes in levels of ESBPIII in cells, tissues or bodily fluids compared with levels of ESBPIII in preferably the same cells, tissues, or bodily fluid type of a normal human control, wherein a change in levels of ESBPIII in the patient versus the normal human control is associated with a gynecologic cancer.

Further provided is a method of diagnosing a metastatic gynecologic cancer in a patient which is not known to have metastasized by identifying a human patient suspected of having a gynecologic cancer that has metastasized; analyzing a sample of cells, tissues, or bodily fluid from such patient for ESBPIII; and comparing the ESBPIII levels in such cells, tissues, or bodily fluid with levels of ESBPIII in preferably the same cells, tissues, or bodily fluid type of a normal human control, wherein an increase in ESBPIII levels in the patient versus the normal human control is associated with a gynecologic cancer which has metastasized.

Also provided by the invention is a method of staging gynecologic cancers in a human by identifying a human patient having a gynecologic cancer; analyzing a sample of cells, tissues, or bodily fluid from such patient for ESBPIII; comparing ESBPIII levels in such cells, tissues, or bodily fluid with levels of ESBPIII in preferably the same cells, tissues, or bodily fluid type of a normal human control, wherein an increase in ESBPIII levels in the patient versus the normal human control is associated with a cancer which is progressing and a decrease in the levels of ESBPIII is associated with a cancer which is regressing or in remission.

Further provided is a method of monitoring gynecologic cancers in a human having such cancer for the onset of metastasis. The method comprises identifying a human patient having such cancer that is not known to have metastasized; periodically analyzing a sample of cells, tissues, or bodily fluid from such patient for ESBPIII; comparing the ESBPIII levels in such cells, tissue, or bodily fluid with levels of ESBPIII in preferably the same cells, tissues, or bodily fluid type of a normal human control, wherein an increase in ESBPIII levels in the patient versus the normal human control is associated with a cancer which has metastasized.

Further provided is a method of monitoring the change in stage of a gynecologic cancer in a human patient by monitoring levels of ESBPIII in the patient. The method comprises identifying a human patient having a gynecologic cancer; periodically analyzing a sample of cells, tissues, or bodily fluid from such patient for ESBPIII; comparing the ESBPIII levels in such cells, tissue, or bodily fluid with levels of ESBPIII in preferably the same cells, tissues, or bodily fluid type of a normal human control sample, wherein an increase in ESBPIII levels in the patient versus the normal human control is associated with a cancer which is progressing and a decrease in the levels of ESBPIII is associated with a cancer which is regressing or in remission.

Further provided are antibodies which specifically bind ESBPIII or fragments of such antibodies which can be used to detect or image localization of ESBPIII in a patient for the purpose of detecting or diagnosing a disease or condition. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. These antibodies or fragments thereof can also be used as therapeutic agents in the treatment of diseases characterized by expression of a ESBPIII. In therapeutic applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to diagnostic assays and methods, both quantitative and qualitative for detecting, diagnosing, monitoring, staging and prognosticating cancers by comparing levels of ESBPIII with those of ESBPIII in a normal human control. What is meant by levels of ESBPIII as used herein, means levels of the native protein expressed by the gene comprising the polynucleotide sequence of SEQ ID NO: 1. The protein encoded by this polynucleotide is depicted in SEQ ID NO: 2. In the alternative, what is meant by levels of ESBPIII as used herein, means levels of the native mRNA encoded by the gene comprising the polynucleotide sequence of SEQ ID NO: 1 or levels of the gene comprising the polynucleotide sequence of SEQ ID NO:1. Such levels are preferably measured in at least one of cells, tissues and/or bodily fluids, including determination of normal and abnormal levels. Thus, for instance, a diagnostic assay in accordance with the invention for diagnosing overexpression of ESBPIII protein compared to normal control bodily fluids, cells, or tissue samples may be used to diagnose the presence of cancers, in particular gynecologic cancers including breast, uterine, ovarian and endometrial cancer.

All the methods of the present invention may optionally include measuring levels of other cancer markers as well as ESBPIII. Other cancer markers, in addition to ESBPIII, useful in the present invention will depend on the cancer being tested and are known to those of skill in the art.

Diagnostic Assays

The present invention provides methods for diagnosing the presence of a gynecologic cancer such as uterine, breast, endometrial or ovarian cancer by analyzing for changes in levels of ESBPIII in cells, tissues or bodily fluids compared with levels of ESBPIII in cells, tissues or bodily fluids of preferably the same type from a normal human control, wherein a change in levels of ESBPIII in the patient versus the normal human control is associated with the presence of a gynecologic cancer.

Without limiting the instant invention, typically, for a quantitative diagnostic assay a positive result indicating the patient being tested has cancer is one in which cells, tissues or bodily fluid levels of a cancer marker, such as ESBPIII, are at least two times higher, and most preferably are at least five times higher, than in preferably the same cells, tissues or bodily fluid of a normal human control.

The present invention also provides a method of diagnosing the onset of metastasis of gynecologic cancers in a patient having a gynecologic cancer which has not yet metastasized. In the method of the present invention, a human cancer patient suspected of having a gynecologic cancer which may have metastasized (but which was not previously known to have metastasized) is identified. This is accomplished by a variety of means known to those of skill in the art.

In the present invention, determining the presence of ESBPIII levels in cells, tissues or bodily fluid, is particularly useful for discriminating between a gynecologic cancer which has not metastasized and a gynecologic cancer which has metastasized. Existing techniques have difficulty discriminating between gynecologic cancers which have metastasized and gynecologic cancers which have not metastasized. However, proper treatment selection is often dependent upon such knowledge.

In the present invention, the cancer marker level measured in such cells, tissues or bodily fluid is ESBPIII. Measure ESBPIII levels in a human patient are compared with levels of ESBPIII in preferably the same cells, tissue or bodily fluid type of a normal human control. That is, if the cancer marker being observed is ESBPIII in serum, this level is preferably compared with the level of ESBPIII in serum of a normal human control. An increase in the ESBPIII in the patient versus the normal human control is associated with a gynecologic cancer which has metastasized.

Without limiting the instant invention, typically, for a quantitative diagnostic assay a positive result indicating the cancer in the patient being tested or monitored has metastasized is one in which levels of a cancer marker such as ESBPIII in cells, tissues or bodily fluid from the patient are at least two times higher, and most preferably are at least five times higher, than in preferably the same cells, tissues or bodily fluid of a normal human control.

Normal human control as used herein includes a human patient without cancer and/or non cancerous samples from the patient; in the methods for diagnosing or monitoring for metastasis, normal human control may preferably also include samples from a human patient that is determined by reliable methods to have uterine, breast, ovarian or endometrial cancer which has not metastasized.

Staging

The invention also provides a method of staging a gynecologic cancer in a human patient. The method comprises identifying a human patient having such cancer and analyzing cells, tissues or bodily fluid from the patient for ESBPIII. The measured ESBPIII levels in such cells, tissues or bodily fluid from the patient are then compared with levels of ESBPIII in preferably the same cells, tissues or bodily fluid type of a normal human control, wherein an increase in ESBPIII levels in the human patient versus the normal human control is associated with a cancer which is progressing and a decrease in the levels of ESBPIII is associated with a cancer which is regressing or in remission.

Monitoring

Further provided is a method of monitoring gynecologic cancers in a human patient having such cancer for the onset of metastasis. The method comprises identifying a human patient having such cancer that is not known to have metastasized; periodically analyzing cells, tissues or bodily fluid from such human patient for ESBPIII; and comparing the ESBPIII levels in such cells, tissues or bodily fluid with levels of ESBPIII in preferably the same cells, tissues or bodily fluid type of a normal human control, wherein an increase in ESBPIII levels in the human patient versus the normal human control is associated with a cancer which has metastasized.

Further provided by this invention is a method of monitoring the change in stage of a gynecologic cancer in a human patient having such cancer. The method comprises identifying a human patient having such cancer; periodically analyzing cells, tissues or bodily fluid from such human patient for ESBPIII; comparing the ESBPIII levels in such cells, tissues or bodily fluid with levels of ESBPIII in preferably the same cells, tissues or bodily fluid type of a normal human control, wherein an increase in ESBPIII levels in the human patient versus the normal human control is associated with a cancer which is progressing in stage and a decrease in the levels of ESBPIII is associated with a cancer which is regressing in stage or in remission.

Monitoring patients for onset of metastasis is periodic and preferably done on a quarterly basis. However, this may be more or less frequently depending on the cancer, the particular patient, and the stage of the cancer.

Assay Techniques

Assay techniques that can be used to determine levels of gene expression (including protein levels), such as ESBPIII in the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to ESBPIII, preferably a monoclonal antibody. In addition, a reporter antibody generally is prepared which also binds specifically to ESBPIII. The reporter antibody is attached to a detectable reagent such as radioactive, fluorescent or enzymatic reagent. For example, horseradish peroxidase enzyme or alkaline phosphatase are routinely used as detectable reagents.

To carry out the ELISA, antibody specific to ESBPIII is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time ESBPIII binds to the specific antibody attached to the polystyrene dish. Unbound sample is washed out with buffer. A reporter antibody specifically directed to ESBPIII and linked to a detectable reagent such as horseradish peroxidase is placed in the dish resulting in binding of the reporter antibody to any monoclonal antibody bound to ESBPIII. Unattached reporter antibody is then washed out. Reagents for peroxidase activity, including a calorimetric substrate are then added to the dish. Immobilized peroxidase, linked to ESBPIII antibodies, produces a colored reaction product. The amount of color developed in a given time period is proportional to the amount of ESBPIII protein present in the sample. Quantitative results typically are obtained by reference to a standard curve.

A competition assay can also be employed wherein antibodies specific to ESBPIII are attached to a solid support and labeled ESBPIII and a sample derived from the host are passed over the solid support. The amount of label detected which is attached to the solid support can be correlated to a quantity of ESBPIII in the sample.

Nucleic acid methods can also be used to detect ESBPIII mRNA as a marker for gynecologic cancers such as uterine, breast, endometrial and ovarian cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to detect the expression of and quantitate the level of expression of that gene. In this approach, a cDNA encoding the ESBPIII gene is fixed to a substrate. The substrate may be of any suitable type including but not limited to glass, nitrocellulose, nylon or plastic. At least a portion of the DNA encoding the ESBPIII gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including, Ads but not limited to, radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts (homogenates or solubilized tissue) obtained from a patient including tissue biopsy and autopsy material. Bodily fluids useful in the present invention include blood, urine, saliva or any other bodily secretion or derivative thereof. Blood can include whole blood, plasma, serum or any derivative of blood.

In Vivo Antibody Use

Antibodies against ESBPIII can also be used in vivo in patients suspected of suffering from gynecologic cancers such as ovarian, breast, endometrial and uterine cancer. Specifically, antibodies against a ESBPIII can be injected into a patient suspected of having a gynecologic cancer for diagnostic and/or therapeutic purposes. The use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. One. 1991 9:631–640). Antibodies with paramagnetic ions as labels for use in magnetic resonance imaging have also been described (Lauffer, R. B. Magnetic Resonance in Medicine 1991 22:339–342). Antibodies directed against ESBPIII can be used in a similar manner. Labeled antibodies against ESBPIII can be injected into patients suspected of having a gynecologic cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

For patients diagnosed with a gynecologic cancer, injection of an antibody against ESBPIII can also have a therapeutic benefit. The antibody may exert its therapeutic effect alone. Alternatively, the antibody is conjugated to a cytotoxic agent such as a drug, toxin or radionuclide to enhance its therapeutic effect. Drug monoclonal antibodies have been described in the art for example by Garnett and Baldwin, Cancer Research 1986 46:2407–2412. The use of toxins conjugated to monoclonal antibodies for the therapy of various cancers has also been described by Pastan et al. Cell 1986 47:641–648. Yttrium-90 labeled monoclonal antibodies have been described for maximization of dose delivered to the tumor while limiting toxicity to normal tissues (Goodwin and Meares Cancer Supplement 1997 80:2675–2680). Other cytotoxic radionuclides including, but not limited to Copper-67, Iodine-131 and Rhenium-186 can also be used for labeling of antibodies against ESBPIII.

Antibodies which can be used in these in vivo methods include both polyclonal, monoclonal or omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

The examples are carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied, the target RNA levels for one sample were used as the basis for comparative results (calibrator) Quantitation relative to the "calibrator" is obtained using the standard curve method or the comparative method (User Bulletin #2: ABI PRISM 7700 Sequence Detection System).

To evaluate the tissue distribution, and the level of ESBPIII in normal and tumor tissue, total RNA was extracted (A from normal tissues, tumor tissues, and from tumors and the corresponding matched normal tissues. Subsequently, first strand cDNA was prepared with reverse transcriptase and the polymerase chain reaction was done using primers and Taqman probe specific to ESBPIII. The results are analyzed using the ABI PRISM 7700 Sequence Detector. The absolute numbers are relative levels of expression of ESBPIII compared to the calibrator tissue.

The absolute numbers depicted in Table 1 are relative levels of expression of ESBPIII in 12 normal different tissues. All the values are compared to normal mammary gland (calibrator). These RNA samples are commercially available pools, originated by pooling samples of a particular-tissue from different individuals.

TABLE 1

Relative Levels of ESBPIII Expression in Pooled Samples

| Tissue | NORMAL |
|---|---|
| Brain | 0 |
| Heart | 0 |
| Kidney | 0 |
| Liver | 0 |
| Lung | 0 |
| Breast | 1 |
| Prostate | 0 |
| Small Intestine | 0 |
| Spleen | 0 |
| Testis | 1 |
| Thymus | 0 |
| Uterus | 59 |

The relative levels of expression in Table 1 show that the highest level of expression of ESBPIII mRNA is in uterus (59), with expression also in mammary gland (1), and testis (1). These results establish that ESBPIII mRNA expression is highly specific for uterus and breast in gynecologic tissues, and testis for male tissues.

The absolute numbers in Table 1 were obtained analyzing pools of samples of a particular tissue from different individuals. They can not be compared to the absolute numbers originated from RNA obtained from tissue samples of a single individual in Table 2.

The absolute numbers depicted in Table 2 are relative levels of expression of ESBPIII in 55 pairs of matching samples, ovarian cancer samples from 5 different individuals, and normal ovarian samples from 5 different individuals. All the values are compared to normal mammary gland (calibrator). A matching pair is formed by mRNA from the cancer sample for a particular tissue and mRNA from the normal adjacent sample for that same tissue from the same individual.

TABLE 2

Relative Levels of ESBPIII Expression in Pooled Samples

| Sample ID | Tissue | Cancer Tissue | Normal Adjacent Tissue | Normal Tissue |
|---|---|---|---|---|
| End10479 | Endometrium 1 | 0 | 2 | |
| End8911 | Endometrium 2 | 1413 | 274 | |
| Endo12XA | Endometrium 3 | 19 | 9 | |
| Endo28XA | Endometrium 4 | 1680 | 174 | |
| Endo3AX | Endometrium 5 | 4 | 4 | |
| Endo5XA | Endometrium 6 | 97 | 454 | |
| Endo65RA | Endometrium 7 | 192 | 12 | |
| Endo8XA | Endometrium 8 | 1 | 485 | |
| End8963 | Endometrium 9 | 1413 | 4 | |
| End4XA | Endometrium 10 | 1 | 0 | |
| End68X | Endometrium 11 | 984 | 1714 | |
| Bld32XK | Bladder 1 | 0 | 0 | |
| Bld46XK | Bladder 2 | 0 | 0 | |
| ClnAS45 | Colon 1 | 0 | 0 | |
| ClnRC01 | Colon 2 | 1 | 3 | |
| ClnB34 | Colon 3 | 0 | 0 | |
| CvxKS52 | Cervix 1 | 0 | 0 | |
| CvxNKS18 | Cervix 2 | 0 | 0 | |
| CvxNKs80 | Cervix 3 | 0 | 0 | |
| Kid107XD | Kidney 1 | 0 | 1 | |
| Kid106XD | Kidney 2 | 2 | 1 | |
| Liv15XA | Liver 1 | 0 | 0 | |
| Liv94XA | Liver 2 | 0 | 0 | |
| Lng60XL | Lung 1 | 0 | 1 | |
| LngC20X | Lung 2 | 0 | 0 | |
| Mam47XP | Breast 1 | 1 | 0 | |

TABLE 2-continued

Relative Levels of ESBPIII Expression in Pooled Samples

| Sample ID | Tissue | Cancer Tissue | Normal Adjacent Tissue | Normal Tissue |
|---|---|---|---|---|
| Mam82XI | Breast 2 | 0 | 2 | |
| MamA06X | Breast 3 | 1 | 0 | |
| MamB011X | Breast 4 | 0 | 0 | |
| Mam59X | Breast 5 | 0 | 0 | |
| Mam162X | Breast 6 | 0.03 | 0.14 | |
| Mam19DN | Breast 7 | 133.09 | 2.04 | |
| Mam220 | Breast 8 | 0.48 | 0.27 | |
| Mam76DN | Breast 9 | 0.51 | 10.46 | |
| MamS079 | Breast 10 | 0.07 | 0.12 | |
| MamS127 | Breast 11 | 0.52 | 0.44 | |
| MamS621 | Breast 12 | 0.07 | 0.39 | |
| Pan71XL | Pancreas 1 | 0 | 0 | |
| Pan82XP | Pancreas 2 | 0 | 0 | |
| Pro18XB | Prostate 1 | 0.0 | 0.3 | |
| Pro20XB | Prostate 2 | 3.3 | 1.3 | |
| Pro69XB | Prostate 3 | 0 | 0.3 | |
| Pro90XB | Prostate 4 | 0 | 0 | |
| Pro65XB | Prostate 5 | 0 | 3 | |
| SmInt21XA | Small Intestine 1 | 0 | 0 | |
| SmInH89 | Small Intestine 2 | 0 | 0 | |
| StoAC44 | Stomach 1 | 0 | 4 | |
| StoAC99 | Stomach 2 | 2 | 5 | |
| Tst39X | Testis 1 | 0 | 0 | |
| Utr135XO | Uterus 1 | 19 | 14 | |
| Utr141XO | Uterus 2 | 25 | 3 | |
| Utr85XU | Uterus 3 | 1148 | 680 | |
| Ovr103X | Ovary 1 | 111 | 0 | |
| Ovr130X | Ovary 2 | 0 | 3 | |
| Ovr1005 | Ovary Cancer 1 | 28 | | |
| Ovr1040 | Ovary Cancer 2 | 60 | | |
| Ovr1157 | Ovary Cancer 3 | 109 | | |
| Ovr63A | Ovary Cancer 4 | 0 | | |
| Ovr1028 | Ovary Cancer 5 | 0 | | |
| Ovr230A | Ovary Normal 1 | | | 0 |
| Ovr32RA | Ovary Normal 2 | | | 0 |
| Ovr40G | Ovary Normal 3 | | | 0 |
| Ovr35GA | Ovary Normal 4 | | | 0 |
| Ovr9RA | Ovary Normal 5 | | | 0 |

0 = Negative

In the analysis of matching samples, the higher levels of expression for ESBPIII were in uterus, endometrium, ovary, and breast. This pattern shows a high degree of specificity for female gynecologic tissues, especially for endometrium, uterus, and ovary. These results confirmed the tissue specificity results obtained with the panel of normal pooled samples (Table 1) for uterus and breast.

Furthermore, the levels of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 2 shows overexpression of ESBPIII in 6 primary endometrial cancer tissues compared with their respective normal adjacent (endometrium samples #2, 3, 4, 7, 9 and 10). There was overexpression in the cancer tissue for 54.54% of the endometrial matching samples tested (total of 11 endometrium matching samples).

ESBPIII is differentially expressed in the four matching samples for uterine cancer. All four samples analyzed showed overexpression in cancer. Of twelve breast cancer matching samples analyzed, five showed underexpression of ESBPIII (#2, 6, 9, 10 and 12) in cancer, whereas five had higher levels of ESBPIII in cancer compared to the normal adjacent tissue (#1, 3, 7, 8, and 11). Two of the breast matching samples do not show expression of ESBPIII mRNA.

ESBPIII is differentially expressed in the two matching samples for ovarian cancer. Sample #1 shows upregulation for the mRNA of ESBPIII in cancer, whereas sample #2 shows overexpression in the normal adjacent tissue. In addition to the two matching samples, ten additional samples for ovary were analyzed including five cancer samples and five normal ovary tissue samples from different individuals. Expression of ESBPIII mRNA was observed in three of the cancer samples (#1, 2, and 3). The median expression in the ovary cancer samples was 28.1, whereas expression in the normal ovary samples was 0.

Altogether, the high level of tissue specificity for gynecological tissues, plus the mRNA differential expression in several of the primary uterus, endometrial, breast, and ovarian matching samples tested is indicative of ESBPIII being a diagnostic marker for gynecologic cancers including uterine, endometrial, breast, and ovarian cancer.

What is claimed is:

1. A method for detecting the presence of uterine or ovarian cancer in a patient comprising:
   (a) measuring levels of ESBPIII comprising a polynucleotide sequence of SEQ ID NO:1 in cells or tissues in a patient; and
   (b) comparing the measured levels of ESBPIII with levels of ESBPIII in cells or tissues from a normal human control, wherein an increase in measured levels of ESBPIII in said patient versus normal human control is associated with the presence of uterine or ovarian cancer.

2. The method of claim 1 wherein the cancer is uterine cancer.

3. The method of claim 1 wherein the cancer is ovarian cancer.

4. The method of claim 1 therein the levels of ESBPIII are measured in cells.

5. The method of claim 1 wherein the levels of ESBPIII are measured in tissues.

6. The method of claim 1 wherein the cancer is uterine cancer and the levels of ESBPIII are measured in cells.

7. The method of claim 1 wherein the cancer is uterine cancer and the levels of ESBPIII are measured in tissues.

8. The method of claim 1 wherein the cancer is ovarian cancer and the levels of ESBPIII are measured in cells.

9. The method of claim 1 wherein the cancer is ovarian cancer and the levels of ESBPIII are measured in tissues.

* * * * *

UNITED STATES PATENT AND TRADEMARK OFFICE
CERTIFICATE OF CORRECTION

| | | |
|---|---|---|
| PATENT NO. | : 7,014,996 B1 | |
| APPLICATION NO. | : 09/806302 | |
| DATED | : March 21, 2006 | |
| INVENTOR(S) | : Roberto A. Macina | |

It is certified that error appears in the above-identified patent and that said Letters Patent is hereby corrected as shown below:

At Column 9, Line 53: Please delete "(A".

At Column 11, TABLE 2-continued: Please insert into the TABLE between lines 30 and 31 the following row:

-- Utr23XU  Uterus 4  1013  60--

At Column 14 in CLAIMS, Claim 4: Please delete "therein" and insert --wherein--.

Signed and Sealed this

Eighteenth Day of December, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 476
<212> TYPE: DNA
<213> ORGANISM: Homo sapiens

<400> SEQUENCE: 1
acgagctgcc acgcacgact gaacacagac agcagccgcc tcgccatgaa gctgctgatg      60
gtcctcatgc tggcggccct cctcctgcac tgctatgcag attctggctg caaactcctg     120
gaggacatgg ttgaaaagac catcaattcc gacatatcta tacctgaata caaagagctt     180
cttcaagagt tcatagacag tgatgccgct gcagaggcta tgggggaaatt caagcagtgt     240 ttcctcaacc agtcacatag aactctgaaa aactttggac tgatgatgca tacagtgtac     300
```

-continued

```
gacagcattt ggtgtaatat gaagagtaat taactttacc caaggcgttt ggctcagagg      360
gctacagact atggccagaa ctcatctgtt gattgctaga aaccactttc ttcttgtgtt      420 gcttttatg tgggaactgc tagacaactg ttgaaacctc aattcattcc atttca          476
```

<210> SEQ ID NO 2
<211> LENGTH: 95
<212> TYPE: PRT
<213> ORGANISM: Homo sapiens

<400> SEQUENCE: 2

```
Met Lys Leu Leu Met Val Leu Met Leu Ala Leu Leu Leu His Cys
 1               5                  10                  15

Tyr Ala Asp Ser Gly Cys Lys Leu Leu Glu Asp Met Val Glu Lys Thr
                20                  25                  30

Ile Asn Ser Asp Ile Ser Ile Pro Glu Tyr Lys Glu Leu Leu Gln Glu
            35                  40                  45

Phe Ile Asp Ser Asp Ala Ala Ala Glu Ala Met Gly Lys Phe Lys Gln
    50                  55                  60

Cys Phe Leu Asn Gln Ser His Arg Thr Leu Lys Asn Phe Gly Leu Met
65                  70                  75                  80

Met His Thr Val Tyr Asp Ser Ile Trp Cys Asn Met Lys Ser Asn
                85                  90                  95
```